(12) United States Patent
Øgreid et al.

(10) Patent No.: US 6,440,661 B1
(45) Date of Patent: *Aug. 27, 2002

(54) METHOD FOR DETECTION OF KR-RAS MUTATIONS AND KIT TO PERFORM IT

(75) Inventors: Dagfinn Øgreid, Bønes; Arve Ulvik, Solheimsvik, both of (NO); Jan Jacob Koornstra, Enschede (NL)

(73) Assignee: UNIFOB, Bergen (NO)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/068,805

(22) PCT Filed: Nov. 15, 1996

(86) PCT No.: PCT/NO96/00271

§ 371 (c)(1),
(2), (4) Date: Aug. 28, 1998

(87) PCT Pub. No.: WO97/19191

PCT Pub. Date: May 29, 1997

(30) Foreign Application Priority Data

Nov. 17, 1995 (NO) .................................................. 954667

(51) Int. Cl.[7] .......................... C12Q 1/68; C12P 19/34; C07H 21/04
(52) U.S. Cl. .......................................... 435/6; 435/91.2
(58) Field of Search .................. 435/6, 91.2; 536/23.1, 536/24.3

(56) References Cited

U.S. PATENT DOCUMENTS 5,910,246 A * 6/1999 Walter et al. ................ 210/232

FOREIGN PATENT DOCUMENTS

| WO | WO 93/20235 | 10/1993 |
| WO | WO 93/22456 | 11/1993 |

OTHER PUBLICATIONS

Suzuki et al., Oncogene, vol. 5, pp 1037–1043, Jan. 1990.*
Krause et al., Electrophoresis, vol. 15, pp 557–561, Jan. 1994.*
Hayashi, PCR Methods and Applications, vol. 1, pp 34–38, Jan. 1990.*
Steve S. Sommer, M.D. Ph.D., et al.; "A Novel Method for Detecting Point Mutations or Polymorphisms and Its Application to Population Screening for Carriers of Phenylketonuria"; *Mayo Clinic Proc*; Nov. 1989; vol. 64, pp. 1361–1372.
Suzuki et al.; "Detection of ras gene mutations in human lung cancers by single–strand conformation polymorphism analysis of polymerase chain reaction products"; *Dialog Information Services file 154, MEDLINE, Dialog accession No. 07419402*; Jul. 1990.

Arve Ulvik et al.; "Detection of Ki–ras mutations in faeces of patients with curable colorectal tumours"; *Journal of the Norwegian Medical Association*; 1995; pp. 3266–3270.
Sidney J. Winawer et al.; "Colorectal Cancer Screening"; *J. National Cancer Institute*; Feb. 20, 1991; vol. 83, pp. 243–253.
Yoshikazu Hasegawa et al; "Detection of K–ras mutations in DNAs isolated from feces of patients with colorectal tumors by mutant–allele–specific amplification (MASA)"; *Oncogene*; 1995; pp. 1441–1445.
J. Smith–Ravin et al.; "Detection of c–Ki–ras mutations in faecal samples from sporadic colorectal cancer patients"; *Gut*; 1995; pp. 81–86.
David Sidransky et al. ; "Identification of ras Oncogene Mutations in the Stool of Patients with Curable Colorectal Tumors"; *Science*; 1992; vol. 256, pp. 102–105.
Johannes L. Bos et al.; "Prevalence of ras gene mutations in human colorectal cancers"; *Nature*; May 28, 1987; vol. 327, pp. 293–297.
Kathleen Forrester et al.; "Detection of high incidence of K–ras oncogenes during human colon tumorigenesis"; *Nature*; May 28, 1987; vol. 327, pp. 298–303.
Johannes L. Bos; "ras Oncogenes in Human Cancer: A Review"; *Cancer Research*; Sep. 1, 1989; pp. 4682–4689.
Glenna C. Burmer et al.; "Analysis of c–Ki–ras Mutations in Human Colon Carcinoma by Cell Sorting, Polymerase Chain Reaction, and DNA Sequencing"; *Cancer Research*; Apr. 15, 1989; pp. 2141–2146.
Bert Vogelstein M.D. et al.; "Genetic Alternations During Colorectal–Tumor Development"; *New England Journal of Medicine*; Sep. 1, 1988; vol. 319, pp. 525–532.
Gabriel Capella et al.; "Frequency and Spectrum of Mutations at Codons 12 and 13 of the C–K–ras Gene in Human Tumors"; *Environmental Health Perspectives*; 1991; vol. 93, pp. 125–131.
J. Breivik et al.; "K–ras mutation in colorectal cancer: relations to patient age, sex and tumour location"; *Br. J. Cancer*; 1994; pp. 367–371.

(List continued on next page.)

Primary Examiner—W. Gary Jones
Assistant Examiner—Jehanne Souaya
(74) Attorney, Agent, or Firm—Merchant & Gould P.C.

(57) ABSTRACT

Method for detecting Ki-ras mutations in exon I, codon 12 to 13 in samples of tissue, tumor tissue, tissue secretions, excretions, expectorates, blood and lymph by two subsequent PCR amplifications comprising a regular PCR amplification and an allele specific amplification and wherein the identification step may comprise a Phast Gel SSCP, characterized in that by a specific selection of oligoprimers in the combination of two PCR amplifications and the Phast Gel identification or in the combination of the said regular PCR amplification and Phast Gel identification produced direct detection of the mutations is produced.

1 Claim, 4 Drawing Sheets

OTHER PUBLICATIONS

Figure 1:

Peter Moerkerk et al.; "Type and Number of Ki–ras Point Mutations Relate to Stage of Human Colorectal Cancer"; *Cancer Research*; 1994; pp. 3376–3378.

Leaonard G. Davis et al.; "Basic Methods in Molecular Biology"; New York: Elsevier; 1986; pp. 320–323.

R. Sepp et al.; "Rapid techniques for DNA extraction from routinely processed archival tissue for use in PCR"; *J. Clin. Pathol.*; 1994; pp. 318–323.

Graham R. Taylor; "Polymerase chain reaction: basic principles and automation"; *In: McPherson MJ, Quirke P, Taylor GR, eds. PCT: a practical approach*; Oxford: Oxford University Press; 1992; pp. 1–14.

A. Rolfs, et al.; "PCR: Clinical Diagnostics and Research"; Berlin, Springer–Verlag; 1992; pp. 1–22.

Richard M. Myers, et al.; "Detection of single base substitutions in total genomic DNA"; *Nature*; Feb. 7, 1985; vol. 313, pp. 495–498.

Edward Winter, et al.; "A method to detect and characterize point mutations in transcribed genes: Amplification and overexpression of the mutant c–Ki–ras allele in human tumor cells"; *Proc. Natl. Acad. Sci.*; Nov. 1985; vol. 82, pp. 7575–7579.

Matty Verlaan–de Vries, et al.; "A dot–blot screening procedure for mutated ras oncogenes using synthetic oligodeoxynucleotides"; *Gene*; 1986; pp. 313–320.

Thomas Ehlen, et al.; "Detection of ras point Mutations by Polymerase Chain Reaction Using Mutation–Specific, Inosine–Containing Oligonucleotide Primers"; *Biochem. Biophys. Res. Comm.*; 1989; vol. 160, No. 2, pp. 441–447.

Youichi Suzuki, et al.; "Detection of ras gene mutations in human lung cancers by single–strand conformation polymophism analysis of polymerase chain reaction products"; *Oncogene*; 1990; pp. 1037–1043.

Belinda J.F. Rossiter, et al.; "Molecular Scanning Methods of Mutation Detection"; *Journal of biological Chemistry*; 1990; vol. 265, No. 22, pp. 12753–12756.

S. Levi, et al.; "Multiple K–ras Codon 12 Mutations in Cholangiocarcninomas Demonstrated with a Senstitive Polymerase Chain Reaction Technique"; *Cancer Research*; Jul. 1, 1991; pp. 3497–3502.

Natalia S. Pellegata, et al.; "Detection of K–ras Mutations by Denaturing Gradient Gel Electrophoresis (DGGE): A Study on Pancreatic Cancer"; *Anticancer Research*; 1992; pp. 1731–1736.

Masato Orita, et al.; "Rapids and Sensitive Detection of Point Mutations and DNA Polymorphisms Using the Polymerase Chain Reaction"; *Genomics*; 1989, pp. 874–879.

Masato Orita, et al.; "Detection of polymorphisms of human DNA by gel electrophoresis as single–strand conformation polymorphisms"; *Proc. Natl. Acad. Sci.*; Apr. 1989; vol. 86, pp. 2766–2770.

Kenshi Hayashi; "PCR–SSCP: A Simple and Sensitive Method for Detection of Mutations in the Genomic DNA"; *PCR Methods Appl.*; 1991; pp. 34–38.

A. Rolfs, et al.; "PCT: Clinical Diagnostics and research"; Berlin: Springer–Verlag; 1991; pp. 163–167.

A. Ulvik, et al.; "Dectection and Identification of Ki–ras Exon 1 Mutations by Minigel Single–Strand Conformation Polymorphism"; *Analytical Biochemistry*; 1995; pp. 137–138.

Dan Y. Wu, et al.; "Allele–specific enzymatic amplification of β–globin genomic DNA for diagnosis of sickle cell anemia"; *Proc. Natl. Acad. Sci.*; Apr. 1989; vol. 86, pp. 2757–2760.

Steve S. Sommer, et al.; "PCR Amplification of Specific Alleles (PASA) is a General Method for Rapidly Detecting Known Single–Base Changes"; *BioTechniques*; 1992; pp. 82–87.

Cynthia D.K. Bottema, et al.; "PCR Amplification of specific alleles: Rapid detection of known mutations and polymorphisms"; *Mutation Research*; 1993; pp. 93–102.

C.R. Newton, et al.; "Analysis of any point mutation in DNA. The amplification refractory mutation system (ARMS)"; *Nuc. Acids Research*; 1989; vol. 17, No. 7, pp. 2503–2516.

Kathleen Porter–Jordan, et al.; "Nested Polymerase Chain Reaction Assay for the Detection of Cytomegalovirus Overcomes False Positive Caused by Contamination With Fragmented DNA"; *Journal of Medical Virology*; 1990; pp. 85–91.

Peter Simmonds, et al.; "Human Immunodeficiency Virus–Infected Individuals Contain Provirus in Small Numbers of Peripheral Mononuclear Cells and at Low Copy Numbers"; *Journal of virology*; Feb. 1990; p. 864–872.

Kathleen Porter–Jordan, et al.; "Source of contamination in polmerase chain reaction assay"; *The Lancet*; May 19, 1990; p. 1220.

Richard T. D'Aquila, et al.; "Maximizing sensitivity and specificity of PCR by pre–amplification heating"; *Nucleic Acids research*; 1991; vol. 19, No. 13, p. 3749.

Quin Chou, et al.; "Prevention of pre–PCR mis–priming and primer dimerization improves low–copy–number amplifications"; *Nucleic Acids Research*; 1992; vol. 20, No. 7, pp. 1717–1723.

Cuthbert E. Dukes; "The Classification of Cancer of the Rectum"; *J. Pathol. Bacteriol.*; 1932; pp. 323–332.

J.W. Lampe, et al.; "Sex differences in colonic function: a randomised trial"; *Gut*; 1993; pp. 531–536.

Carlos Caldas, et al.; "Detection of K–ras Mutations in the Stool of Patients with Pancratic Adenocarcinoma and Pancratic Ductal Hyperplasia"; *Cancer Research*; Jul. 1, 1994; pp. 3568–3573.

Kenshi Hayashi; "PCR–SSCP: A Method for Detection of Mutations"; *Genet. Anal. Tech.*; 1992; pp. 73–79.

Asako Takahashi–Fujii, et al.; "Practical Application of Fluorescence–based Image Analyzer for PCR Single–stranded Conformation Polymorphism Analysis used in Detection of Multiple Point Mutations"; *PCR Methods and Applications*; 1993; pp. 323–327.

L.H. Trumper, et al.; "Diagnosis of pancreatic adenocarcinoma by polymerase chain reaction from pancreatic secretions"; *BR. J. Cancer*; 1994; pp. 278–284.

* cited by examiner

METHOD FOR DETECTION OF KR-RAS MUTATIONS AND KIT TO PERFORM IT

The invention relates to a method for detecting mutations in samples of tissue and stool by PCR amplification using specific oligoprimers and a kit to perform the method.

An increasing body of evidence implicates somatic mutations as causally important in the induction of human cancers. These somatic mutations may accumulate in the genomes of previously normal cells, some of which may then demonstrate the phenotypes associated with malignant growth. Such oncogenic mutations may include a number of different types of alterations in DNA structure, including deletions, translocations and single nucleotide alterations. The latter, also known as point mutations, may frequently intervene in carcinogenesis, in that a variety of mutagenic chemicals induce such mutations. In addition, such mutations may occur spontaneously as a result of mistakes in DNA replication.

Advances in recombinant DNA technology have led to the discovery of normal cellular genes (proto-oncogenes and tumor suppressor genes) which control growth, development, and differentiation. Under certain circumstances, regulation of these genes is altered and they cause normal cells to assume neoplastic growth behavior. There are over 100 known protooncogenes and suppressors genes to date, which fall into various categories depending on their functional characteristics. These include, (1) growth factors and growth factors receptors, (2) messengers of intracellular signal transduction pathways, for example, between the cytoplasm and the nucleus, and (3) regulatory proteins influencing gene expression and DNA replication.

Point mutations have been directly implicated in the causation of many human tumors. Some tumors carry oncogenes of the ras gene family, which differ from their normal cellular counterpart protooncogenes by the presence of a point mutation at one of a limited number of sites in these genes. Similarly, point mutations in critical regions of tumor suppressor genes, such as p53, are often detected in tumor cells. These mutations represent qualitative changes in the tumor cell genome which distinguish these cells from normal cells and provide a basis for diagnosis of the genetic origin of a tumor under study. Identification of the mutations that have created active oncogenes may provide important diagnostic and prognostic clues for tumor development. For example, a number of mutations have been found to alter the 12th codon of the ras oncogenes, causing replacement of a normally present glycine by any of a number of alternative amino acid residues. Such amino acid substitutions create a potent transforming allele. Thus, the presence of a particular nucleotide substitution may be a strong determinant of the behavior of the tumor cell (e.g., its rate of growth, invasiveness, etc.). As a result, DNA probes of oncogene mutations have promise as diagnostic reagents in clinical oncology.

Among the various types of neoplasms, a number of those which are found in the gastrointestinal tract are associated with oncogenic mutations. This association is particularly significant for pancreatic and colorectal cancer. Colorectal cancer is the third most common malignancy in the world, with more than 700,000 new cases expected in 1996. In the United States alone, over 70,000 people will die from colorectal cancer in this same year. While patients with advanced disease have a very poor prognosis, colorectal tumors diagnosed at any stage prior to metastatis can usually be cured by surgical or colonoscopic excision. A method to detect surgically resectable tumors could, therefore, considerably reduce deaths from this disease (Winawer, et al., J. National Cancer Institute, 83:243, 1991).

A method to detect mammalian nucleic acid in stool is known from WO93/20235 (Vogelstein, B. & Kinzler, K.). This method comprises purification of faeces and two different methods for amplification of mutated ras genes. Method 1 is based upon PCR amplification of Ki-ras and subsequent cloning of the amplified Kir-ras into a bacterial phage, culturing the phage and plaque hybridizing with oligonucleotide probes which are specific for the single mutations in Ki-ras. Method 2 is based upon PCR amplification, followed by gel electrophoresis of the PCR product, hybridization of the product to the nylon filter and allele specific hybridization with isotope labeled probes, specific for each mutation. Both methods are sensitive and specific. Unfortunately these methods are both time consuming and labour intensive, since all mutations in Ki-ras are not detected by one method. More than 10 mutations of Ki-ras in exon I are already described. The above methods use gene probes specific for each of these mutations. If a stool sample shall be screened and a pirori it is not known which mutation is present, a great number of different probes has to be used in each sample, and in addition each probe has to be isotopically labeled.

PCR amplification of DNA from stool is also known from Smith-Ravin et al. (Gut, 35, 81–86, (1995)). In this procedure 10–50 g stool is used and DNA was extracted, then purified DNA was amplified using mitochondrial primers and analysed for ras mutations using an allele specific mismatch method. Total detection rate was 9 of 22, the method used great amounts of stool and was not suitable for screening since it was necessary to use specific mutant allele specific amplification (MASA) probes to detect the mutations.

In an article in Oncogene, 10, 1441–45, (1995) Hasegawa et al. have amplified DNA from 15 patients out of 19 and by using standard MASA technique, identified 3 mutations. Following this a special MASA-technique was performed, which resulted in detected mutations in 10 patients. The problem with this procedure is a low detection rate and that a specific probe has to be used for each mutation. Thus the method is not suitable for screening analysis.

Suzuki, Y. et al. (Oncogene, 5 (7): 1037–43, 1990 describes detection of ras gene mutations in human lung cancers by single stranded conformation polymorphism (SSCP) analysis of polymerase chain reaction (PCR) products. This method did, however not indicate the sequences of the mutations.

The objects of the present invention is to produce a screening procedure for detection of Ki-ras mutations in tissues and stool, with adequate specificity and simplicity to perform, using small amounts of substrate.

These objects are obtained by the present invention characterized by the enclosed claims.

The present invention is related to a screening procedure for detection of Ki-ras mutations in small samples of tissue or stool in which specific primers according to the invention is used to generate a PCR product of 221 base pairs. This product shows unique single stranded conformation polymorphism (SSCP) patterns in which each mutation is detected and identified using SSCP analyses performed on 20% homogenous polyacrylamide gels (polyacrylimide Phast™ Gel, Pharmacia).

To increase the amount of the PCR product it is possible to perform subsequently semi-nested PCR in which an extra oligonucleotide was used in the 5' end while the specific oligoprimer of the first step was used in the 3' end. In the next PCR cyclus both oligoprimers from the first step was used which resulted in the 221 base pair PCR product In this product the mutations were detected as above with Phast gel SSCP.

Still another increase of the sensitivity according to the invention is obtained by in a third step using allele specific amplification or mutation specific primer extension. This step involves using probes containing a mismatch against the wild type gene on the last base in the 3' end and an additional mismatch on base no. 2 or 3 from the 3' end. This strategy surprisingly increased the sensitivity of the method. Thus by using the method according to the invention Ki-ras mutations were detected in 8 patients of 12 using double PCR and in another study 6 patients with mutations in Ki-ras of 7 patients were detected by the first step while the 7 with mutations was detected by combining step 1 and 2. Thus the detection rate was 90% with single PCR and 100% with combined PCR.

In the following the invention is disclosed in detail together with examples and figures.

FIG. 1 exhibits SSCP-analysis of Ki-ras exon 1. Lane 1: Wild type, (the wild type sequence of codons 12 and 13 is GGT and GGC respectively). Lane 2 to 7: Samples heterozygous for wild type and the codon 12 mutations: 2: AGT, 3: CGT, 4: TGT, 5: GAT, 6: GCT, and 7: GTT. Lane 8: A sample heterozygous for wild type, and the codon 13 mutation GAC. Lane 9: A sample heterozygous for wild type and a rare double mutation of codon 12: TTT.

Figure 2:
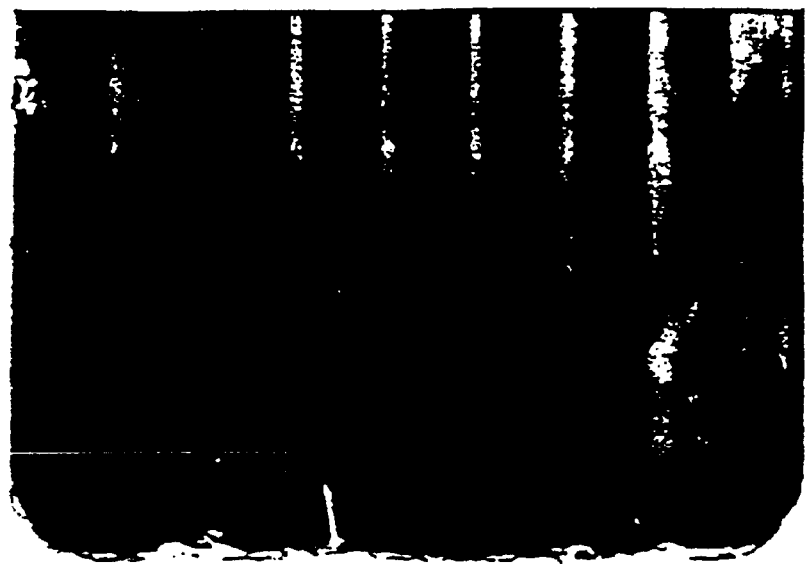

FIG. 2 shows PCR-SSCP analysis of exon I of the Ki-ras gene from surgical specimens. All samples were heterozygous except for the sample in lane 1. Wild type codon 12 is GGT, and codon 13 GGC. Electrophoresis was run on polyacrylimide Phast™ Gel homogenous 20.

Codon 12 mutations are shown in the following lanes: 1: AGT (wild type allele is missing); lane 2: CGT; lane 3: TGT; lane 4: GAT; lane 5: GCT; lane 6: GTT; lane 8: TTT. Lane 7 shows a codon 13 mutation: GAC.

Figure 3:
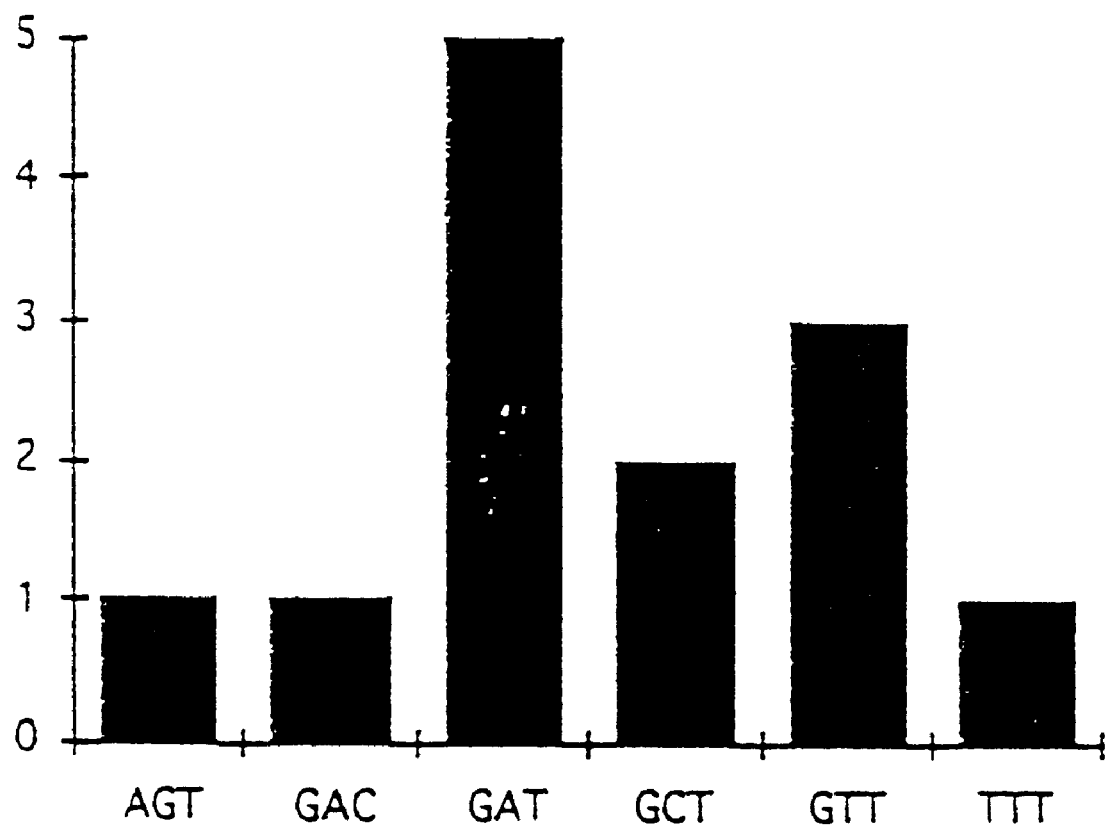

FIG. 3 shows frequencies of the different mutations found in the tumours.

Figure 4:
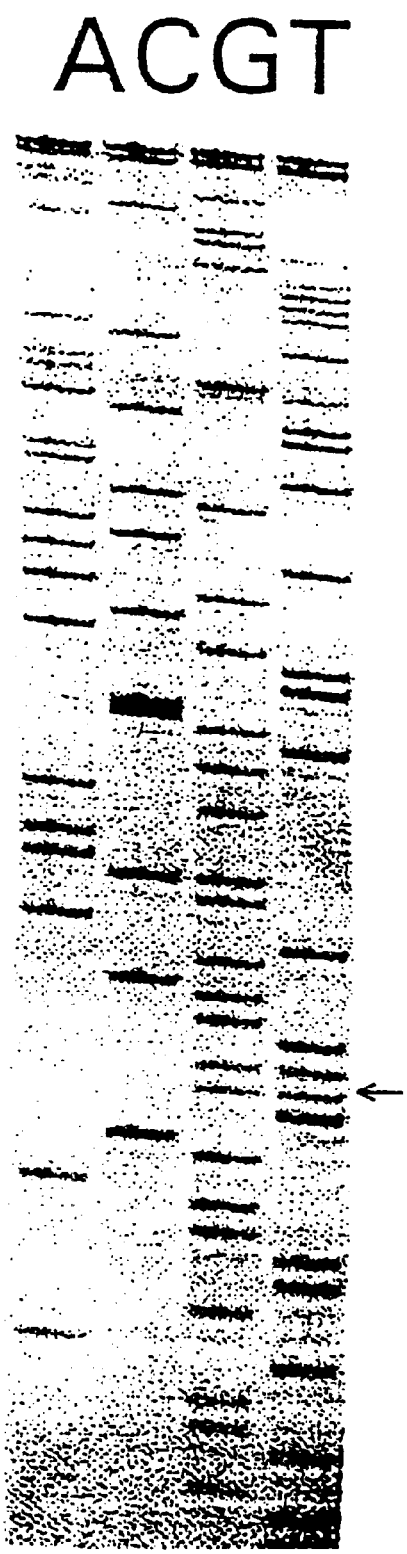

FIG. 4 exhibits sequence analysis of adenoma 1 from patient C-05. DNA sequence analysis of exon 1 from Ki-ras shows two G to T transitions in codon 12 (arrow).

Figure 5:
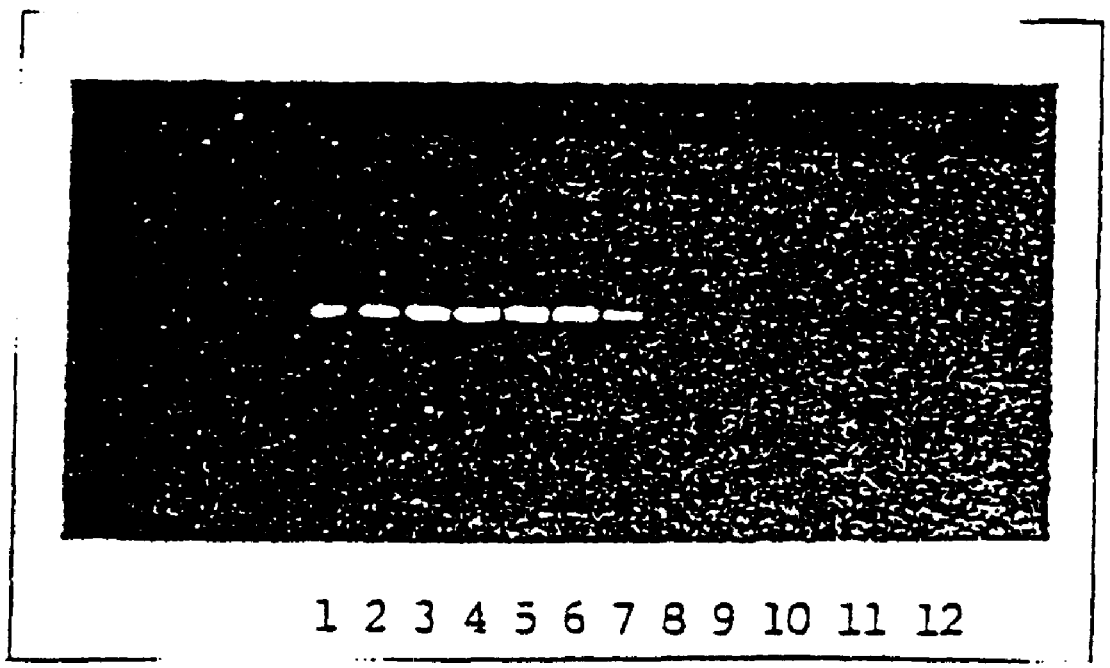

FIG. 5 exhibits gel electrophoresis of PCR products of ASA analysis (discriminant PCR) of DNA purified from faeces. The signals show positive GTT mutation. 1 and 2: Patient CO4, 3 and 4: Patient C-23, 5 and 6: Positive control, 7: Positive control diluted 1:100, 8 and 9: Negative control (faeces from patient with another mutation than that tested for), 12: Negative control (DNA not added).

The present invention relates to a method of detecting a nucleic acid having a mutant nucleotide sequence present in stool, wherein the presence of the altered nucleic sequence is associated with neoplasia of the gastrointestinal tract.

In its broadest sense, the present invention allows the detection of any target nucleic acid sequence of diagnostic or therapeutic relevance, where the target nucleic acid sequence is present in stool. Thus, the target nucleotide sequence may be, for example, a mutant nucleotide, a restriction fragment length polymorphism (RFLP), a nucleotide deletion, a nucleotide substitution, or any other mammalian nucleic acid sequence of interest.

In one embodiment, the method of the invention is applicable for detection of mutant nucleotide sequences associated with benign as well as malignant neoplasias. In a preferred embodiment, neoplasia of the gastrointestinal tract, including both the small and large intestine, pancreas, and stomach, is detected, although the method can be used to detect any neoplastic mutant nucleotide sequence, regardless of origin, as long as the sequences is detectably present in stool.

Benign neoplasias of the small intestine include adenomas, leiomyomas, lipomas, and angiomas, whereas large intestine benign neoplasias are primarily adenomatous polyps. The malignant neoplasias of the small intestine include adenocarcinomas, leiomyosarcomas, lymphomas, and carcinoid tumors. In the case of the large intestine and colon, colorectal carcinoma is the most common malignant neoplasia identified.

Numerous nucleic acids having mutant nucleotide sequences that produce an abnormal gene product are known to be associated with various neoplasias. Among the most common mutant nucleotide sequences are oncogenes and tumor suppressor genes, such as MCC, DCC, APC, FAP, p53, and various DNA repair enzymes. Of special significance in the present invention is the detection of the Ki-ras mutant oncogene.

In order to analyze stool specimens according to the method of the invention, it is necessary to separate the mammalian nucleic acid present in the specimen. There are two primarily problems associated with the preparation of mammalian nucleic acid from stool. First, the mammalian nucleic acid must be liberated from the mammalian cells and separated from bacterial cells. This step is further complicated by the fact that it is desireable to avoid releasing nucleic acid from the bacterial cells, since there is such a huge excess of bacterial nucleic acid compared to eukaryotic nucleic acid in the stool specimen. Secondly, once liberated, the mammalian nucleic acid can be protected from the relatively high concentration of nucleases which are present in stool and which could degrade the liberated mammalian nucleic acid and thereby preclude its analysis. In the present invention, it has been found that these stringent criteria can be met by incubating the stool with a commersially available lysis buffer which contains a high concentration of buffer of at least about 500 mM, at a pH of at least about 8.0, containing a chelating agent such as EDTA, and a relatively low salt concentration, preferably less than 10 mM.

The stool lysis buffer minimizes nucleic degradation by virtue of the pH and chelating properties, lyses eukaryotic cells, but not bacterial cells, and is suitable for further processing to purify and/or concentrate the eukaryotic nucleic acid. After treatment with lysis buffer, the specimen is processed (e.g. by centrifugation) to remove bacteria and other unwanted residues. The non-particulate fraction of the lysate is then incubated with a proteinase (such as 0.5 $\mu$g/ml proteinase K) in SDS (1%) to degrade nucleases and other proteins. The nucleic acid in the sample can be further separated by chemical means, such as binding the negatively charged nucleic acid to iron exchanged columns, and there after eluting purified/concentrated and/or concentration of DNA can be performed by precipitation with ethanol.

In addition, it has been found that stool also contains inhibitors which are preferably removed if the mutant nucleotide sequence present in the stool nucleic acid is to be amplified, such as by polymerase chain reaction (PCR). One of these inhibitors interferes with DNA amplification by Taq polymerase. This inhibitor can be removed by binding the stool nucleic acid to a stationary matrix in the presence of chaotropic salts, such as 6.0 M sodium iodide or sodium perchlorate. Surprisingly, it has been found that glass is the preferred matrix for this purpose. Especially preferred commercial versions of glass are Prep-A-gene™ (Bio-Rad) and Spin-Bind™ (FMC).

The other inhibitor present in stool prevents the binding of nucleic acid to glass. It has been found that this second inhibitor can be removed by binding the inhibitor to a modified ion-exchange resin (e.g. Qiagen) in the presence of high salt concentrations such as at least about 1.0 M. Those of skill in the art can envision various ways that the above described process for concentrating and/or purifying mammalian DNA from stool specimens can be modified once it is recognized that mammalian nucleic acid can be selectively obtained from stool specimens. Alternatively, those of skill in the art can ascertain, without undue experimentations, alternative reagents and conditions which are functionally equivalent to those described herein, now that it is known that such methods are practicable on stool specimens. Such modifications and functional equivalents are embraced by the present invention.

Amino acids referred to herein may be identified according to the following three-letter or one-letter abbrevations:

| Amino | Three-Letter Abbreviation | One-Letter Abbreviation |
|---|---|---|
| L-Alanine | Ala | A |
| L-Arginine | Arg | R |
| L-Asparagine | Asn | N |
| L-Aspartic Acid | Asp | D |
| L-Cysteine | Cys | C |
| L-Glutamine | Gln | Q |
| L-Glutamic Acid | Glu | E |
| L-Glycine | Gly | G |
| L-Histidine | His | H |
| L-Isoleucine | Ile | I |
| L-Leucine | Leu | L |
| L-Lysine | Lys | K |
| L-Methionine | Met | M |
| L-Phenylalanine | Phe | F |
| L-Proline | Pro | P |
| L-Serine | Ser | S |
| L-Threonine | Thr | T |
| L-Tryprophan | Trp | W |
| L-Tyrosine | Tyr | Y |
| L-Valine | Val | V |

When it is desired to amplify the mutant nucleotide sequence before detection, this can be accomplished using oligonucleotide(s) which are primers for amplification. These unique oligonucleotide primers are based upon identification of the flanking regions contiguous with the mutant nucleotide sequence. For example, in the case of Ki-ras, these oligonucleotide primers comprise sequence which are capable of hybridizing with the flanking nucleotide sequence 5'-GGTGGAGTATTTGATAGTGTATTAACCTTATGT-3' (Seq. id. no. 1) and/or 5'-AATGGTCCTGCACCAGTAAT-3'(Seq. id. no. 2) and sequences complementary thereto.

The primers which can be used according to the method of the invention embrace oligonucleotides of sufficient length and appropriate sequence so as to provide initiation of polymerization of a significant number of nucleic acid molecules containing the target nucleic acid. In this manner, it is possible to selectively amplify the specific target nucleic acid sequence containing the nucleic acid of interest. Specifically, the term "primer" as used herein refers to a sequence comprising two or more deoxyribonucleotides or ribonucleotides, preferably at least eight, which sequence is capable of initiating synthesis of a primer extension product, which is substantially complementary to a target nucleic acid strand. The oligonucleotide primer typically contains 15–22 or more nucleotides, although it may contain fewer nucleotides.

Experimental conditions conductive to synthesis include the presence of nucleotide triphosphates and an agent for polymerization, such as DNA polymerase, and a suitable temperature and pH. The primer is preferably single stranded. If double stranded, the primer is first treated to separate its strands before using to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition.

Primers used according to the method of the invention are designed to be "substantially" complementary to each strand of mutant nucleotide sequence to be amplified. Substantially complementary means that the primers must be sufficiently complementary to hybridize with their respective strands under conditions which allow the agent for polymerizatioin to function. In other words, the primers should have sufficient complementary with the flanking sequences to hybridize therewith and permit amplification of the mutant nucleotide sequence. Preferably, the terminus of the primer that is extended has perfectly base paired complementary with the complementary flanking strand.

Oligonucleotide primers used according to the invention are employed in any amplification process that produces increased quantities of target nucleic acid. Typically, one primer is complementary to the negative (−) strand of the mutant nucleotide sequence and the other is complementary to the positive (+) strand. Annealing the primers to denatured nucleic acid followed by extension with an enzyme, such as the thermostable or Taq DNA polymerase and nucleotides or ligases, results in newly synthesized + and − strands containing the target nucleic acid. Because these newly synthesized nucleic acids are also templates, repeated cycles of denaturing, primer annealing, and extention results in exponential products or the region (i.e. the target mutant nucleotide sequence) defined by the primer. The product of the amplification reaction is a discrete nucleic acid duplex with termini corresponding to the ends of the specific primers employed. Those of skill in the art will know of other amplification methodologies which can also be utilized to increase the copy number of target nucleic acid.

A useful way of increasing the number of copies of described PCR product is to employ the method called semi-nested PCR. Using this approach, one of the original primers are being used as a new primer, e.g., flagging the 3'-region of the first PCR product. Another upstream primer, e.g., 5'-AACTTATGTGTGACATGTTCTAAT-3' (Seq. id. no. 3) can then be used in the opposite flagging region to generate a new, smaller PCR product that contains the positive mutated retion within the newly famed PCR product.

The oligonucleotide primers for use in the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (Tetrahedron Letters, 22:1859–1862, 1981). One method for synthesizing oligonucleotides on a modified solid support is described in U.S. Pat. No. 4,458,066. One method of amplification which can be used according to this invention is the polymerase chain reaction (PCR) described in U.S. Pat. Nos. 4,683,202 and 4,683,195.

Any stool specimen nucleic acid, in purified or nonpurified form, can be utilized as the starting nucleic acid or acids, provided it contains, or is suspected of containing, the specific nucleic acid sequence containing the target nucleic acid. Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The mutant nucleotide sequence to be amplified, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

Where the target mutant nucleotide sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means; the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases of by the enzyme RecA, which has helicases activity, and in the presence of riboATP, is known to denature DNA. The reaction conditions suitable for strand separation of nucleic acids with helicases are described by Kuhn Hoffmann-Berling (CSH-Quantitative Biology, 43:63, 1978) and techniques for using RecA are reviewed in C. Radding (Ann. Rev. Genetics, 16:405–437, 1982).

If the nucleic acid containing the target nucleic acid to be amplified is single stranded, its complement is synthesized by adding one or two oligonucleotide primers. If a single primer is utilizied, a primer extension products is synthesized in the presence of primer, an agent for polymerization, and the four nucleoside triphosphates described below. The product will be complementary to the single-stranded nucleic acid and will hybridize with a single-stranded nucleic acid to form a duplex of unequal length strands that may then be separated into single strands to produce two single separated complementary strands. Alternatively, two primers may be added to the single-stranded nucleic acid and the reaction carried out as described.

When complementary strands of nucleic acid or acids are separated regardless or whether the nucleic acid was originally double or single-stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7–9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

In some amplification embodiments, the substrates, for example, the deoxyribonucleotide triphosphates dATP, dCTP, dGTP, and dTTP, are added to the synthesis mixture, either separately or together with the primers, in adequate amount and the resulting solution is heated to about 90°–100° C. from about 10 minutes, preferably from 1 to 4 minutes. After this heating period, the solution is allowed to cool to rom temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature. The agent for polymerization may be any compound or system which will function to accomplish the synthesis of primer extension products, including enzymes. Suitable enzymes for this purpose include, for example, *E. coli* DNA polymerase I, Taq polymerase, Klenow fragment of *E. coli* polymerase I, T4 DNA polymerase, other available DNA polymerases, polymerase muteins reverse transcriptase, ligase, and other enzymes, including heat-stable enzymes (i.e. those enzymes which perform primer extension after being subjected to temperatures sufficiently elevated to cause denaturation). Suitable enzymes will facilitate combination of the nucleotides in the proper manner to form the primer extension products which are complementary to each mutant nucleotide strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above. In any event, the method of the invention is not to be limited to the embodiments of amplification which are described herein.

The newly synthesized mutant nucleotide strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The above process is repeated on the single-stranded molecules. Additional agent for polymerization, nucleotides, and primers may be added, if necessary, for the reaction to proceed under the conditions prescribed above. Again, the synthesis will be initiated one end of each of the oligonucleotide primers and will proceed along the single-strands of the template to produce additional nucleic acid. After this step, half of the extension product will consist of the specific nucleic acid sequence bounded by the two primers.

The steps of denaturing and extension products synthesis can be repeated as often as needed to amplified the target mutant nucleotide sequence to the extent necessary for detection. The amount of the mutant nucleotide sequence produced will accumulate in an exponential fashion.

The amplified product may be detected and identified by analysing it by single-stranded confirmational polymorphism using the Pharmacia Phast System for Automatic Temperature Controlled Electrophoresis and Silverstaining. In such a process, for example a small sample of amplified DNA is subjected to denaturation there after electrophoraced on a precasted phast-gel, for example those supplied from Pharmacia. In a gel like this a single-stranded DNA fragment will migrate depending on its confirmation. The confirmation is dependent on the primer sequence of nucleotides, and sequences that vary by one or several nucleotides will contain a specific unique confirmation.

In an embodiment of the invention, nucleotide fragments from stool, after amplification, are separated into fragments of different confirmation by gel electrophoresis on Pharmacia polyacrylimide Phast™ gels. After electrophoration, the gel are exposed to a mixture containing silver to stain the various nucleotide fragments, thereby detecting and identifying various types of mutant nucleotide fragments.

EXAMPLE 1
Detection and Identification of Ki-ras Exon 1 Mutations by Minigel Single-strand Conformation Polymorfism Single-strand conformation polymorphism (SSCP) is a convenient method for detecting mutations (40). The method relies on the fact that the conformation assumed by a single-stranded DNA fragment under non-denaturing conditions, and thus its mobility in electrophoresis, depends on its exact base sequence. With SSCP, the mutation normally remains to be identified after it has been detected. However, in the case of the oncogene Ki-ras, there is a limited number of mutations reported, the majority of which are confined to codons 12 and 13 of exon 1. Thus, provided that each mutational variant has a characteristic SSCP-pattern, there will be a basis for identification. This has been indicated in some previous articles on Ki-ras (18, 41, 42).

This study describes a SSCP-protocol where all of the commonly reported mutational variants of Ki-ras exon 1 are detectable and identifiable. Furthermore, two other variants, to our knowledge not previously reported in surgical biopsy material, were also detected. The protocol utilizes precast polyacrylamide gels, and an automatic electrophoresis and staining instrument (Phast System, Pharmacia, Sweden). No isotopic labelling of DNA is involved.

Polymerase chain reactions (PCR) were carried out on a Perkin Elmer TC 1 thermocycler using a two step profile; 94° C., 15 sec, 58° C., 30 sec, for 30–40 cycles depending on the amount of template. This profile was preceded by 2 min. at 94° C. and ended by 5 min. at 72° C. The primers used were: 5'AACCTTATGTGTGACATGTTCTAAT-3' (Seq. id. no. 4) (upstream) and 5'-AATGGTCCTGCACCAGTAAT3' (Seq. id. no. 2) (downstream). The PCR reaction mix consisted of 10 mM Tris-HCl pH 9.0, 50 mM KCl, 1.5 mM $MgCl_2$, 0.01% (w/v) gelatin, 0.1% Triton, 125 $\mu$M of each dNTP, 0.2 $\mu$M of each primer and 0.2 $\mu$M of Taq polymerase (Supertaq, HT Biotechnology Ltd., UK) in a total volume of 100 $\mu$l. The product size was 221 bp.

SSCP protocol: 4 $\mu$l of the PCR products were denatured by mixing with an equal volume of the ionised formamide and heating briefly to 80° C. Subsequent rapid cooling on ice was not necessary to keep in the DNA in a denatured state. The samples were applied to a 20% homogenous polyacrylamide gel (Phast™ gel) with buffer strips containing 0.88 M L-Alanine, 0.25 M Tris pH 8.8, and run with the following program: prerun: 400 V, 10 mA, 2.5 W, 15° C., 100 Vh, loading: 400 V, 1 mA, 2.5 W, 15° C., 3 Vh, separation: 400 V, 10 mA, 2.5 W, 15° C., 300 Vh. After electrophoresis, the gels were silver stained according to the manufacturer's instructions. Using this procedure, 24 samples could be analysed in two hours.

All of the seven most commonly reported Ki-ras exon 1 mutations (7) and an unusual double mutation (Codon 12: GGT to TTT) proved detectable and identifiable by the method presented (FIG. 1). The mutations were all found when screening a number of lung, colon, and pancreas tumour biopsies (n>400). The identy of the mutations were established by sequencing at least two samples representing an individual type of banding pattern. In addition, further samples were analysed with the technique of allele specific amplification (ASA) (20) as a control. In each case, the mutations appeared as two bands (or sometimes more, due to secondary bands presumably representing metastable conformations) in addition to the wild type bands. This was interpreted to mean that both mutated single-strands migrated differently from the wild type single-strands. It was thus possible to distinguish between different mutational variants and occasional PCR-produced unspecific bands relative to two wild type specific bands). This was considered to be a requisite for a reliable identification.

The minimum ratio of mutated versus normal DNA required for the mutation to be detectable was tested by the following: Genomic DNA with a homozygous AGT mutation was mixed with normal genomic DNA in the ratios: 1:10, 1:20, 1:40, 1:80, and 1:160 with the combined amounts held constant and equal to 250 ng. These mixtures were then used as templates in a PCR reaction of 35 cycles. Thereafter, SSCP analysis were carried out on the PCR products. The mutation signal was detectable in all of the samples, but only with difficulty when the mixing ratio (mutant/normal DNA) was 1:160 (results not shown).

In addition to the aforementioned mutations, a mutation in the last base of codon 19: TTG to TTT, found in a colon cancer biopsy, was also detectable and distinguishable from the other mutations (not shown).

It should be cautioned that using SSCP to identify mutations is possible only in special cases were a limited spectrum of specific mutations are reported to occur. In the case presented, the demonstrated heterogeneity of the SSCP patterns facilitated fast, simple, and sensitive detection and identification of Ki-ras exon 1 mutations by SSCP alone.

EXAMPLE 2
Detection of Ki-ras Mutations in the Feaces of Patients with Colorectal Tumours, Using PCR
II Materials and Methods
Patients Selection 25 patients admitted between August and November 1994 to the Surgical Department of the University Hospital of Bergen (Haukeland Hospital), Norway, entered the study. We chose to include two different groups, which would enable us to judge the sensitivity of the methods we used. The first group (A) was formed by 10 patients undergoing colonoscopic investigation of suspected colorectal tumours and who where subsequently found to have either a malignant colorectal tumour (carcinoma) or a benign tumour (adenoma) greater than 1 cm in size. The other group (B), consisting of 15 patients, comprised patients who underwent surgical resection of colorectal carcinomas or adenomas greater than 1 cm in size. The patients (10 males, 15 females) were between 49 and 90 years of age (mean age, 70) at the time of tumour extirpation.

Tumour and Faeces Collection

From every patient tumour tissue samples were collected, in most cases directly after surgery and colonoscopy. In the latter instance, tissue samples were obtained through biopsy or polypectomy. From 5 patients, paraffin-embedded tissue blocks were provided by the Department of Pathology of Haukeland Hospital. In total, 27 colorectal tumour specimens were obtained from 25 patients. From two patients we obtained all together four different tumours, that met our criteria; these tumours were found concomitantly in the surgically resected specimens. Of these 27 tumours, 15 were carcinomas and 12 were adenomas, according to the pathology report.

Stool samples were obtained either during colonoscopy, through collection of the washing fluid, or before surgery. The samples were stored at −80° C.

DNA Preparation from Tumour Samples

Genomic DNA was extracted from tumour samples using the following standard methods[10].

Approximately 25 mg of tumour tissue was collected in a 1.5 ml Eppendorf tube. For the purpose of cell lysis, the sample was dissolved in 300 µl of TE buffer (10 mM TrisHCl pH 8.0 and 1 mM EDTA), 30 µl of proteinase XIV (10 mg/ml), 30 µl of 10% SDS (sodiumdodecyl-sulfate) and 30 µl of TNE buffer (100 mM TrisHCl pH 8.0, 1.5 M NaCl and 100 mM EDTA pH 8.0). The samples were incubated overnight at 37° C.

To remove protein and contaminants from the samples phenol/chloroform extractions were performed: to each sample 1 volume of phenol was added, mixed by vortexing, and centrifuged at 4° C., 13000 g for 5 minutes. Then the upper layer was transferred to a new tube after which 1 volume of chloroform was added, the solution was mixed by vortexing, and centrifuged for 5 minutes. The the upper aqueous layer was transferred to a new tube and 2.5 volumes of 96% ethanol were added. After precipitation at −20° C. for at least 1 hour, the sample was centrifuged for 10 minutes, after which the supernatant was carefully discarded. The pellet was washed in 70% ethanol and then air-dried. Finally, the DNA was resuspended in 100 µl of TE buffer.

DNA from paraffin-embedded tissue blocks was extracted using a recently described method[11].

A 20 µm section was cut from the tissue block. The section was suspended in 10 mM TrisHCl pH 9.0 containing 5% Chelex-100 resin (Bio Rad Laboratories, Hercules, Calif., USA) and boiled for 10 minutes.

Polymerase Chain Reaction Procedures

The polymerase chain reaction (PCR) has become established as one of the most widely used techniques of molecular biology. The reasons are the following; it is a rapid, inexpensive and simple means of producing microgram amounts of DNA from minute quantities of source material. The PCR-technique relies on knowledge of at least part of the DNA sequence around the region of interest. We will first briefly describe the basic principles of PCR, before turning to the procedures, implemented in this study.

In PCR, the double-stranded DNA fragment that is to be amplified (template) is mixed with two short single-stranded DNA molecules (primers) which are complementary to sequences at either end of the sequence to be amplified. The reaction mixture also contains a heat-stable DNA polymerase, and the four nucleotides required for DNA synthesis.

The mixture is heated to approximately 95° C. to denature the double-stranded template into single strands, and then cooled to about 60° C. to allow each primer to anneal with its complementary sequence on the single-stranded templates. The temperature is then adjusted to 72° C., the optimal temperature for the polymerase to synthesize new strands, through extension of each primer by successive additions of nucleotides. Each newly synthesized DNA strand will contain a binding site for the other primer, thus serving as an additional template in the next cycle. The cycle is repeated a number of times, each time doubling the amount of product. To give an impression of the amplification strength of PCR, 20 cycles produce one million copies of one DNA molecule[12-13].

Exon 1 of Ki-ras was amplified by PCR under the following conditions: 2 µl of dissolved DNA was amplified in a total volume of 100 µl, containing 10 mM Tris-HCl (H 9.0 at 25° C.), 50 mM KCl, 1.5 mM $MgCl_2$, 0.01% (w/v) gelatin, 0.1% Triton X-100, 125 µM of each deoxynucleotidetriphosphate and 0.5 µM of each primer. 0.2 units of Taq DNA polymerase was added. The Taq polymerase (Supertaq) was purchased from HT Biotechnology Ltd. (Cambridge, England).

The reactions were run on a DNA thermocycler (Perkin-Elmer Cetus, Norwalk, Conn., USA) using a two step profile: 94° C. for 15 seconds (denature), 60° C. for 30 seconds (anneal/extend), for 40 cycles. This profile was preceded by 2 minutes at 94° C. (single denaturation step) and a final extension step for 4 minutes at 72° C. The oligonucleotide primers were as follows: upstream: 5'-AAC CTT ATG TGT GAC ATG TTC TAA T-3' (Seq. id. no. 5) (designated R1) and downstream: 5'-AAT GGT CCT GCA CCA GTA AT-3' (Seq. id. no. 2) (R2). The primers yielded a product of 221 base pairs (bp) length.

Identification of Ki-ras Mutations in Tumour Samples

Several methods exist for determining whether a single-base change exists in amplified DNA[14-21]. Of these, we chose a method that has been shown to be both rapid and sensitive, namely single-strand conformation polymorphism analysis (SSCP)[22-24].

Since DNA is a negatively charged heteropolymer, it will move towards the positive pole when placed in an electric field. This is called electrophoresis.

In the laboratory, the principle of molecular sieving is often employed. With this procedure, one is able to separate a selection of different molecules, e.g. different DNA fragments, by forcing them to move in a network of hydrated organic polymers, called a gel. The moving speeds of the DNA fragments will be retarded according to their size and/or shape.

The technique of SSCP utilises a certain property of small (100–400 bp) single-stranded DNA fragments of equal size: when allowed to fold upon themselves, they will form distinct structures (conformations). These conformations are determined by intramolecular interactions and thus by the sequence. Hence, a point mutation will be reflected as as changed conformation which, under favourable buffer conditions and gel pore size, will result in a changed mobility during electrophoresis. Since complementary strands exhibit different conformations, wild type (normal, unaltered) DNA fragments appear as two bands in the gel. A point mutation will lead to two additional bands[25]. In practice, additional bands often appear, due to alternative conformations.

In this study, electrophoresis of PCR products was performed on precast polyacrylamide mini-gels (Phast™ Gels), using the Pharmacia Phast System (Pharmacia LKB Biotechnology, Uppsala, Sweden).

SSCP protocol: The PCR products were denatured by mixing with formamide and heating to 80° C. for 1 minute. The samples were then applied to a 20% homogenous polyacrylamide gel with Phast™ gel native buffer strips containing 0.88 M L-Alanine, 0.25 M Tris pH 8.8, and run with the following program: prerun: 400 V, 10 mA, 2.5 W, 100 Vh; loading: 400 V, 1 mA, 2.5 W, 3 Vh; separation: 400 V, 10 mA, 2.5 W, 300 Vh. After electrophoresis the gels were silver stained according to the manufacturer's recommendations, and dried.

Using the described method, each mutation in codons 12 and 13 of Ki-ras displayed a distinct band pattern on the polyacrylamide Phast™ gel. The identity of each mutation was established previously by direct sequencing and mutation specific primer extension (MSPE, disussed later)[26]. In this study, these patterns were used as references to establish the type of mutation in the tumour samples.

All tumour samples were analysed for the presence of mutations in exon 1 of the Ki-ras. From those patients whose tumours contained a mutation, we next analysed the faeces samples.

DNA Preparation From Faeces Samples

Genomic DNA from faeces was purified, using the Qiagen cell culture DNA kit (Qiagen Inc., Chatsworth Calif., USA).

Approximately 10 mg of faeces was mixed with 1 ml of the G2 buffer. From a colonoscopic wash we took 500 $\mu$l and added an equal amount of G2 buffer. This buffer lyses the nuclei and denatures all kinds of protein. The stool-lysis buffer mix was vortexed and cleared by centrifugation at 13,000 g for 10 minutes at 4° C. The supernatant was then transferred to a new tube after which 25 $\mu$l of proteinase K (20 mg/ml) was added. The proteinase digests the denatured proteins into smaller fragments. The DNA then is stripped of all bound proteins. After incubation at 50° C. for 60 minutes, Qiagen genomic tips were placed over a waste tray and equilibrated with 1 ml of equilibration buffer QBT. Then the samples were applied onto the equilibrated genomic tips, after which the column was washed with 4×1 ml of the QC wash buffer. The columns were then placed onto clean collection tubes and an appropriate volume of elution buffer QF was added. The DNA was precipitated with 0.7 volumes of isopropanol, manually mixed, centrifuged at 4° C. for 10 minutes at 13000 g and the supernatant was carefully removed. The DNA was washed with ethanol 70% and then repelleted by centrifugation. The samples were air-dried for 10 minutes and finally the pellet was redissolved in 50 $\mu$l of TE buffer.

Detection of Ki-ras Mutations in Faeces Samples

To check the expected mutation within codon 12 or 13 of the Ki-ras gene, we used mutation specific primer extension (MSPE), also called allele specific amplification (ASA)[27-30].

The method of MSPE depends on designing a primer that, in PCR, preferentially will amplify one sequence over an other, even if the sequences differ by only one base. This is realised if the primer completely matches the desired (mutation containing) sequence, but mismatches the other sequence (carrying no mutation), at or near the 3' end. The mismatch between the normal (not mutated) DNA template and the oligonucleotide will result in poor amplification of this normal fragment.

Greater reliability regarding the specificity of MSPE might be achieved if the mutation-specific primer is destabilized by additional deliberate mismatches near the 3' end in such a way that the probability of elongation (thus of amplification), in spite of the mismatch, is even more reduced[31].

Mismatch primers were selected with the aid of a commercial computer program (Oligo 4.0, National Biosciences Inc., USA), including an additional mismatch, a few base pairs away from the 3' end. All primers used in this study were purchased.

For MSPE, we used (semi) nested PCR procedures and AmpliWax gems.

In nested PCR, sensitivity and specificity of DNA amplification are considerably improved[32-34]. The process involves two consecutive PCRs. The first PCR contains a pair of external primers while the second contains two nested primers which are internal to the first primer pair (nested PCR), or one of the first primers and a single nested primer (semi-nested). The larger fragment produced by the first reaction is used as a template for the second PCR.

PCR Ampliwax Gems (Perkin Elmer) facilitate the use of the "hot start" technique. This technique prevents complete mixing of PCR reactant until the reaction has reached a temperature which minimises non-specific annealing of primers to non-target DNA. As a result, specificity and sensitivity of the PCR process are increased and the risk of primer dimerization (primer-primer annealing) is reduced[35, 36].

PCR Procedures

In the first round 5 $\mu$l of dissolved DNA was amplified in the same reaction mixture as the tumour samples, with primer concentrations of 0.2 $\mu$M. The sequence of the upstream primer was: 5'-GGT GGA GTA TTT GAT AGT GTA TTA ACC TTA TGT-3' (R3) (Seq. id. no. 1). The downstream primer was R2 (Seq. id. no. 2). These primers yielded fragments of 244 bp length. After denaturation for 2 minutes at 94° C., PCR was performed for 16 cycles (94° C. for 15 s, 60° C. for 15 s).

The amplifiability of the template in each sample was checked before MSPE was performed.

1 $\mu$l of the PCR product from the first round was reamplified by PCR, using the primers R1 (Seq. id. no. 5) and R2 (Seq. id. no. 2) (0.5 $\mu$M, for 40 cycles (94° C. for 15 s, 60° C. for 30 s). Aliquots of 15 $\mu$l were analysed by electrophoresis on a 3% NuSieve GTG (FMC BioProducts) agarose gel. Those samples from the first round that proved to be amplifiable were subjected to MSPE.

We incorporated AmpliWax gems and the hot start technique in the second PCR round. 1 $\mu$l of the PCR product from the first round was reamplified with the combination of primer R3 (0.2 $\mu$M) and the mutation-specific mismatch primer. The mismatch primers had the following sequences:
GCT: 5'-AAG GCA CTC TTG C;T ACG CTA G-3' (R4);
 (Seq. id. no. 11);
GTT: 5'-AAG GCA CTC TTG CCT ACG CTA A-3' (R5)
 (Seq. id. no. 6);
GAT: 5'-AAG GCA CTC TTG CCT ACG CTA T-3' (R6)
 (Seq. id. no. 7);
GAC: 5'-CGT CAA GGC ACT CTT GCC TAC CT-3' (R7)
 (Seq. id. no. 8);
AGT: 5'-AGG CAC TCT TGC CTA CGC TAT T-3' (R8)
 (Seq. id. no. 9);
TGT: 5'-GCA CTC TTG CCT ACG CCA TA-3' (R9) (Seq. id. no. 10).

The combinations of R3 (Seq. id. no. 1) with the mismatch primers yielded products of 143 (TGT) to 150 (AGT) bp. PCR was performed for 40 cycles (94° C. for 15 s, 60° C. for 30 s), with primer concentrations of 0.2 $\mu$M (R4, R5) (Seq. id. no. 11; Seq. id. no. 6) or 0.4 $\mu$M (R6–R9) (Seq. id. no. 7–10). To check the TTT mutation we found in one tumour we performed both a GTT and TGT mismatch on the faeces sample; only when both series would yield positive results, we could assume that TTT-mutation containing tumour cells were presented in the faeces.

As negative controls, we used DNA from faeces of patients with colorectal tumours without a mutation in codons 12 and 13 of Ki-ras. Those samples with the best amplifiability were chosen, to minimalize the chance of false-positive results. As positive controls, we used DNA from tumours where the type of mutation in Ki-ras that was established by SSCP and confirmed by sequencing. MSPE products were subjected to electrophoresis in a 3% NuSieve agarose gel. Designation of a signal as positive required a distinct intense signal stronger than the negative controls.

Results

A two-step experimental approach was devised. We first analysed colorectal tumours for the precense of Ki-ras mutations. If present, we analysed the faeces from these patients. The results are summarised in table 1.

group A (C-01) was operated soon after colonoscopy so we obtained a pre-surgery sample in addition to the colonoscopy sample.

After purification of DNA from faeces, exon 1 of Ki-ras was PCR-amplified. It soon became clear that colonoscopy-samples contained more human DNA than the pre-surgery-samples. The mechanical effect of washing a fluid around the tumour during colonoscopy apparently provoked the release of cells into the lumen. Hence, both the total amount of cells and the tumor-derived cell-fraction was in general higher in the samples obtained during colonoscopy.

A one-step PCR with 40 cycles, which is normally sufficient for any amount of starting material was apparently

TABLE 1

Characteristics of the patients and tumours studied for mutations in Ki-ras.

| Patient | Sex/Age | Tumour location | Tumour type/Stage# | Tumor mutation | Mutant in faeces## |
|---------|---------|-----------------|--------------------|----------------|-----|
| C-01 | M/79 | Rectum | Carcinoma/B | GGT→GCT (Ala) | I/II: + |
| C-04 | F/69 | Descending colon | Adenoma | GGT→GTT (Val) | I: + |
| C-05 | F/90 | Transverse colon | Adenoma 1 | GGT→TTT (Phe) | II: − |
|  |  | Ascending colon | Adenoma 2 | GGT→GAT (Asp) |  |
| C-09 | F/63 | Ascending colon | Carcinoma/C | GGT→GAT (Asp) | II: + |
| C-12 | F/80 | Rectum | Adenoma | GGT→GAT (Asp) | I: + |
| C-14 | M/71 | Sigmoid | Carcinoma/B | GGT→GAC (Asp) | II: + |
| C-16 | F/75 | Sigmoid | Carcinoma/C | GGT→GAT (Asp) | II: − |
| C-17 | M/87 | Sigmoid | Carcinoma/C | GGT→AGT (Ser) | II: − |
| C-18 | F/77 | Sigmoid | Carcinoma/B | GGT→GTT (Val) | I: + |
| C-23 | M/80 | Sigmoid | Carcinoma/B | GGT→GTT (Val) | II: + |
| C-24 | F/68 | Rectum | Carcinoma/B | GGT→GAT (Asp) | II: − |
| C-25 | F/49 | Rectum | Carcinoma/C | GGT→GCT (Ala) | II: + |

Tumours were classified according to Dukes' classical three stage system[71] of CRC (A: tumour confined to the muscularis propria, B: extension through the muscularis propria, but confined to the colon, C: Metastasis to regional lymph nodes).
Faeces samples were collected during colonoscopy (I) or before surgery (II). From patient C-01, both faeces samples I and II were analysed.
Tumour mutations were determined by single-strand conformation polymorphism and electrophoresis on PhastGels ™. Mutations in faeces samples were established with mutation specific primer extension.

Genomic DNA from 27 tumours was analysed for the presence of mutations at the 12th and 13th codon of the Ki-ras gene by the technique of PCR-SSCP. Polyacrylamide gel electrophoresis and silver staining were performed, using the PhastSystem. Band patterns are shown in FIG. 2.

We detected point mutations in 13 tumour samples (48%), that had been obtained from 12 patients (4 from group A, 8 from group B). Mutations were detected in 4 of 12 adenomas (33%, all of the villous type) and 9 of 15 carcinomas (60%). The majority of the mutations was localised in the sigmoid and rectum.

Of the 15 female patients that entered the study, 8 (53%) had a mutation in Ki-ras, whereas 4 of 10 males (40%) were affected. In one patient (C-05), samples obtained from two different adenomas were found to contain different mutations.

The mutation spectrum of the tumours is shown in FIG. 3. The most frequent mutation was GGT to GAT (glycine to aspartic acid) in codon 12, observed in 5 cases. The other mutations we found in the same codon were GGT to GTT (glycine to valine, 3 cases), GGT to GCT (glycine to alanin, 2 cases) and GGT to AGT (glycine to serine, 1 case). We found 1 case of a mutation in codon 13, namely GGC to GAC (glycine to aspartic acid).

One tumour (C-05, adenoma 1) produced an unusual band pattern which resembled a pattern, previously associated with a double mutation in codon 12 (GGT to TTT). Sequence analysis of the PCR product confirmed this double mutation (FIG. 4).

We next analysed the faeces samples from the 12 patients whose tumours contained a mutation. One patient from not sufficient for several of the faeces samples, possibly due to "inhibiting factors" in the faeces. We hoped to increase the efficiency of PCR by diluting these factors by performing nested PCR. This would also increase the amount of template for MSPE.

With this two-step PCR strategy, all faeces samples from both group A and B proved to be amplifiable, thus suited for MSPE. The template for MSPE was 1 μl of the PCR product from the first round. AmpliWax Gems and the hot start technique were incorporated. Positive and negative controls were included.

In this way we confirmed the mutations, found in the respective tumours, in all 4 faeces samples from group A. In the faeces samples, obtained from group B (plus case C-01), we identified the mutation in 5 of the 9 cases. Proximal as well as distal tumours (patient C-09, ascending colon) gave positive results. Four different types of mutations were detected: GCT, GTT, GAT and GAC.

For optimal results, the concentration of the mutation specific primers had to be adjusted to values varying from 0.2 to 0.4 μM.

Representative results of the detection of mutations in Ki-ras in faeces with MSPE are shown in FIG. 5.

Discussion

In this study we investigated the possibility to detect Ki-ras mutations in faeces of patients with colorectal tumours. In 27 tumours (12 adenomas and 15 carcinomas), Ki-ras mutations were found in 13 tumours; 4 in adenomas (33%) and in 9 carcinomas (60%). These frequencies are in accordance with earlier reports[4,5]. This result confirms the potential role of Ki-ras mutations as a relatively early marker of colorectal neoplasia.

It has been recently observed that females have a higher prevalence of Ki-ras-mutations in colorectal cancer than males[8]. It has been proposed that this difference is related to the time of contact with, and the concentration of, particular carcinogens in the faeces. Both bowel transit time and constipation prevalence are reported to be substantially higher in women[38]. A reflection of this sex-difference is visible in our material, where 53% of the tumours in females and 40% of the tumours in males were found to harbour a mutation.

We found the majority of the mutations (12 of 14, when considering TIT as two mutations) to occur at position 2 of codons 12 and 13. This has also been recognized earlier[2,3,6].

Although the number of tumours investigated in this study is small, the total frequency of the three mutations, that are believed to be most common (CAC, GAT and GTT) is surprisingly close to the frequency found in larger series[7,8].

Some point mutations have been associated with distinct anatomical locations[40]. In this respect, our results with the GCT mutation are in agreement with the observation that this mutation seems to be restricted to the rectum.

The correlation of certain types of Ki-ras mutations with the clinical stage, such as the recently described restriction of the GAT mutation to Dukes B staged tumours[9], could not be recognised in our patient material. In fact, of the five tumours with a GAT mutation, two were classified as Dukes C.

We analysed the faeces samples from the 12 patients (from one patient both a colonoscopy and a pre-surgery sample) whose tumours contained a Ki-ras mutation. We were able to identify the corresponding Ki-ras mutation in 9 of 13 (4 colonoscopy and 9 pre-surgery) stool samples. The identification was achieved in all 4 colonoscopy samples and in 5 out of 9 of the pre-surgery samples. Only the latter samples are of diagnostic value. The colonoscopy samples just provided valuable information when evaluating the method.

Although the amplifiability of all the faeces samples had been established, MSPE did not yield positive results in every sample. As a possible explanation, a number of problems can be recognised. First, as mentioned earlier, faeces samples probably differ greatly with respect to both the total mucosal-cell content and the tumour-derived cell-fraction. Second, the purification of human cells from faeces is probably impeded by the presence of bacterial cells. Another problem concerns the fact that human cells are subject to a relatively high concentration of degradative enzymes in the faeces. In addition, faeces has been found to contain certain inhibitors, which interfere with DNA amplification in PCR[1]. By binding DNA to a modified ion-exchange resin (e.g., Qiagen, used in this study), these inhibitors might be removed, at least in part.

The MSPE method as such seems very well suited for the detection of Ki-ras mutations in faeces. The analysis of faeces samples required the detection of mutated Ki-ras sequences derived from the tumour cells among an abundance of wild-type Ki-ras from normal cells. Experiments to establish the sensitivity of the method demonstrated that MSPE could detect at least 0.01% mutated cells in a heterogenous cell population (unpublished data). One other feature of MSPE is that the method is relatively insensitive to "air-carried" pre-PCR contamination (e.g., human DNA released from hair, skin etc.).

Further studies are needed to improve the efficiency of the method, for example by efforts to equalise the starting amount of template for MSPE. Recent experiments in our laboratory indicate that this might be achieved with a three-round PCR set-up. Another improvement might be made by "enriching" the sample with mutant cells before analysis, for example by preferential purification of mutant versus wild-type cells.

Screening for several mutations in one analysis could be possible by the use of a number of mismatch primers simultaneously. Additional investigation of such a so called "Multiplex-PCR" assay would be valuable. Finally, further evaluation of a possible application of the technique in a screening test is needed. Such a test, probably with a high specificity, would give a positive predictive value, far exceeding that of the detection of blood in faeces.

Recently, Ki-ras mutations have also been identified in faeces of patients with pancreatic adenocarcinoma, and its presumed precursor lesions[39]. This finding broadens the potential scope of Ki-ras analysis in faeces even more. Hence, Ki-ras detection in faeces could be a rapid and non-invasive screening strategy, not only for early detection of colorectal cancer but for other gastro-intestinal and pancreatic malignancies as well.

EXAMPLE 3
Ki-ras Oncogene Analysis in the Accurate Diagnosis of Malignant Lesions in Pancreas Activation of the Ki-ras oncogene by specific point mutations at codon 12 occurs at a remarkably high frequency in pancreatic ductal adenocarcinomas and is likely to be an important event in the pathogenesis of this cancer. Ki-ras oncogene mutations are also detectable in pancreatic juice from patients with malignant lesions. This specific gene-activation can thus help in the diagnosis of pancreatic malignancies, in the differential diagnosis against chronic pancreatitis, and also to separate benignant from malignant cystic disease of the pancreas.

We recently developed a rapid non-radioactive SSCP-assay for the detection and identification of Ki-ras mutations with a sensitivity limit (cells with one mutated allele/normal cells) of 0.02. We applied this technique to various samples from thirty patients that were operated for malignant lesion of the pancreas. All thirty patients harboured a codon 12 mutation in the tumour. Pancreatic juice that were collected from twelve patients showed presence of mutation in nine cases. Three patients with pancreatic cystic diseases that originally were classified as non-malignant, showed Ki-ras mutation in cyst fluid and cyst wall biopsies, and a malignant histology was confirmed after operation. Peritoneal fluid, collected from three patients, showed presence of the same mutation as found in the tumour.

The presence of mutations gat and gtt seems to be associated with a better prognosis after operation than presence of all other mutations. We conclude that analysis for Ki-ras mutations in pancreatic lesions can be helpful both diagnostically and prognostically, and can lead to an earlier diagnosis for this devastating disease whose only hope for survival is early diagnosis and radical surgery.

EXAMPLE 4
Association of Specific Ki-ras Gene Mutations with Improved Patient Survival in Pancreatic Adenocarcinoma Pancreatic adenocarcinomas are known to have a high incidence of Ki-ras gene mutations. In the present study, formaline-fixed and paraffin embedded tumour material from 73 patients with primary adenocarcinomas were examined for the presence of activating point mutations in exon 1 of Ki-ras using a single stranded conformation polymorphism-based method. 49 (72%) of the 68 carcinomas which were successfully amplified, harboured one or several point mutations.

Survival analysis showed no correlation between the absence or presence of Ki-ras mutation and patient survival, and no difference between cases with one or several mutations was observed. The presence of two specific mutations (gtt and gat triplets in codon 12), however, was significantly associated with improved patient survival when compared with all other types of mutations or absence of mutation (p=0.0038). In a multivariate survival analysis (Cox' method), including patients age at the time of diagnosis, tumour diameter and tumour localization in addition, type of Ki-ras mutation showed a strong and independent prognostic importance (p=0.03).

Thus, the presence of gtt and gat mutations in exon 1 of Ki-ras define a subgroup of patients with pancreatic adenocarcinomas in whom the prognosis is significantly improved. Molecular analysis of Ki-ras could be a helpful marker to select patients that are more likely to benefit from extensive surgical treatment.

REFERENCES

1. Sidransky D, Tokino, T, Hamilton S R, et al. Identification of ras oncogene mutations in the stool of patients with curable colorectal tumours. Science 1992; 256: 102–105.
2. Bos J L, Fearon E R, Hamilton S R, et al. Prevalence of ras gene mutations in human colorectal cancers. Nature 1987; 327: 293–297.
3. Forrester K, Almoguera C, Han K, et al. Detection of high incidence of Ki-ras oncogenes during human colon tumorigenesis. Nature 1987; 327: 298–303.
4. Bos J L, Ras. oncogenes in human cancer: A review. Cancer Res. 1989; 49: 4682–4689.
5. Burmer G C, Rabinovitch P S, Loeb L A. Analysis of c-Ki-ras mutations in human colon carcinoma by cell sorting, polymerase chain reaction, and DNA sequencing. Cancer Res. 1989; 49: 2141–2146.
6. Vogelstein B, Fearon E R, Hamilton S R, et al. Genetic alterations during colorectal tumour development. N. Eng. J. Med. 1988; 319: 525–532.
7. Capella G, Cronauer-Mitra S, Peinado M A, Perucho M. Frequency and spectrum of mutations at codons 12 and 13 of the c-Ki-ras gene in human tumours. Environ. Health Perspect. 1991; 93: 125–131.
8. Breivik J, Meling G J, Spurkland A, Rognum T O, Gaudernack G. Ki-ras mutation in colorectal cancer: relations to patient age, sex and tumour location. Br. J. Cancer 1994; 69: 367–371.
9. Moerkerk P, Arends J W, van Driel M, de Bruine A, de Goeij A, ten Kate J. Type and number of Ki-ras point mutations relate to stage of human colorectal cancer. Cancer Res. 1994; 54: 3376–3378.
10. Davis L G, Battery J, Dibner M D. Basic methods in molecular biology. New York: Elsevier, 1986: 320–323.
11. Sepp R, Szabó I, Uda H, Sakamoto H. Rapid techniques for DNA extraction from routinely processed archival tissue for use in PCR. J. Clin. Pathology 1994; 47: 518–523.
12. Taylor G R. Polymerase chain reaction: basic principles and automation. In: McPherson M J, Quirke P, Taylor G R, eds. PCR: a practical approach. Oxford: Oxford University Press, 1992: 1–14.
13. Rolfs A, Schuller I, Finckh U, Weber-Rolfs I. PCR: Clinical diagnostics and research. Berlin, Springer-Verlag, 1992: 1–22.
14. Myers R M, Lumelsky N, Lerman L, Maniatis T. Detection of single-base substitutions in total genomic DNA. Nature 1985; 313: 495–498.
15. Winter B, Yamamoto F, Almoguera C, Perucho M. A method to detect and characterize point mutations in transcribed genes: amplification and overexpression of mutant c-Ki-ras allele in human tumour cells. Proc. Natl. Acad. Sci. USA 1985; 82: 7575–7579.
16. Verlaan-de Vries M, Bogaard M E, van den Elst H, van Boom J H, van der Eb A J, Bos J L. A dot-blot screening procedure for mutated ras oncongenes using synthetic oligodeoxynucleotides. Gene 1986; 50: 313–320.
17. Ehlen T, Dubeau L. Detection of ras point mutations by polymerase chain reaction using mutation-specific, inosine-containing oligonucleotide primers. Biochem. Biophys. Res. Comm. 1989; 160: 441–447.
18. Suzuki Y, Orita M, Shiraishi M, Hayashi K, Sekiya T. Detection of ras gene mutations in human lung cancers by single-strand conformation polymorphism analysis of polymerase chain reaction products. Oncogene 1990; 5: 1037–1043.
19. Rossiter B J F, Caskey C T. Molecular scanning methods of mutation detection. J. Biol. Chem. 1990; 265: 12753–12756.
20. Levi S, Urbano-Ispizua A, Gill R, et al. Multiple Ki-ras codon 12 mutations in cholangiocarcinomas demonstrated with a sensitive polymerase chain reaction technique. Cancer Res. 1991; 51: 3497–3502.
21. Pellegata N S, Losekoot M, Fodde R, et al. Detection of Ki-ras mutations by denaturing gradient gel electrophoresis (DGGE): A study on pancreatic cancer. Anticancer Res. 1992; 12: 1731–1736.
22. Orita M, Suzuki Y, Hayashi K. A rapid and sensitive detection of point mutations and genetic polymorphisms using polymerase chain reaction. Genomics 1989; 5: 874–879.
23. Orita M, Iwahana H, Kamazawa K, et al. Detection of polymorphisms of human DNA by gel electrophoresis as single-strand conformation polymorphisms. Proc. Natl. Aca. Sci. 1989; 86: 2766–2770.
24. Hayashi K. PCR-SSCP: A simple and sensitive method for detection of mutations in genomic DNA. PCR Methods Appl. 1991; 1: 34–38.
25. Rolfs A, Schuller I, Finckh U, Weber-Rolfs I. PCR: Clinical diagnostics and research. Berlin: Springer-Verlag 1992: 163–167.
26. Ulvik A. Rapid detection and identification of mutations in exon 1 of Ki-ras by SSCP on the Pharmacia Phast System (manuscript submitted).
27. Sommer S S, Cassady J D, Sobell J L, Bottema C D K. A novel method for detecting point mutations or polymorphisms and its application to population screening for carriers of phenylketonuria. Mayo Clin. Proc. 1989; 64: 1361–1372.
28. Wu D Y, Ugozzoli L, Pal B K, Wallace R B. Allele-specific amplification of β-globin genomic DNA for diagnosis of sickle cell anemia. Proc. Natl. Acad. Sci. USA 1989; 86: 2757–2760.
29. Sommer S S, Groszbach A R, Bottema C D K. PCR amplification of specific alleles (PASA) is a general method for rapidly detecting known single-base mutations. BioTechniques 1992; 12: 82–87.
30. Bottema C D K, Sommer S S. PCR amplification of specific alleles: Rapid detection of known mutations and polymorphisms. Mutation Res. 1993; 288: 93–102.
31. Newton C R, Graham A, Heptinstall L E, et al. Analysis of any point mutation in DNA. The amplification refractory mutation system (ARMS). Nucl. Acids Res. 1989; 17: 2503–2516.
32. Porter-Jordan K, Rosenberg E I, Keiser J F, et al. Nested polymerase chain reaction assay for the detection of cytomegalovirus overcomes false positives caused by contamination with fragmented DNA. J. Med. Virol. 1990; 30: 85–91.

33. Simmonds P, Balfe P, Peutherer J F, Ludlam C A, Bishop J O, Brown A J L. Human immunodefiency virus-infected individuals contain provirus in small numbers of peripheral mononuclear cells and at low numbers. J. Virol. 1990; 64: 864–872.
34. Porter-Jordan K, Garrett C T. Source of contamination in polymerase chain reaction assay. Lancet 1990; 19: 335.
35. D'Aquila R T, Bechtel L J, Videler J A, Eron J J, Gorzyca P, Kaplan J C. Maximizing sensitivity and specific of PCR by preamplification heating. Nucleic Acids Res. 1991; 19: 3749.
36. Chou Q, Russel M, Birch D E, Raymond J, Bloch W. Prevention of pre-PCR dimerization improves low-copy-number amplifications. Nucleic Acids Res. 1992; 20: 1717–1723.
37. Dukes C E. The classification of cancer of the rectum. J. Pathol. Bacteriol. 1932; 35: 323–332.
38. Lampe J W, Fredstrom S B, Slavin J L, Potter J D. Sex differences in colonic function: a randomised trial. Gut 1993; 34: 531–536.
39. Caldas C, Hahn S A, Hruban R H, Redston M S, Yeo C J, Kern S E. Detection of Ki-ras mutations in the stool of patients with pancreatic adenocarcinoma and pancreatic ductal hyperplasia. Cancer Res. 1994; 54: 3568–3573.
40. Hayashi K. (1992) Genet. Anal. Tech. Appl. 9, 73–79.
41. Takahashi-Fujii, Ishino A, Shimada A and Kato I. (1993) PCR Methods Appl. 2, 323–327.
42. Trumper L H, Burger B, von-Bonin F, Hintze A, von-Blohn G, Pfreundschuh M, and Daus H. (1994) Br. J. Cancer. 80, 278–284.

What is claimed is:

1. A method for detecting Ki-ras mutations in exon 1, codon 12 to 13, in a stool sample, the method consisting of:

a) amplifying DNA isolated from the stool sample by a single PCR amplification with primers having the sequences set forth as SEQ ID NO:5 and SEQ ID NO:2; and b) identifying the mutations by SSCP on a 20% homogenous polyacrylamide gel, wherein identification produces a direct detection of the Ki-ras mutations.

* * * * *

SEQUENCE LISTING

```
<160> NUMBER OF SEQ ID NOS: 11

<210> SEQ ID NO 1
<211> LENGTH: 33
<212> TYPE: DNA
<213> ORGANISM: Homo sapiens

<400> SEQUENCE: 1
ggtggagtat ttgatagtgt attaacctta tgt                          33

<210> SEQ ID NO 2
<211> LENGTH: 20
<212> TYPE: DNA
<213> ORGANISM: Homo sapiens

<400> SEQUENCE: 2
aatggtcctg caccagtaat                                         20

<210> SEQ ID NO 3
<211> LENGTH: 24
<212> TYPE: DNA
<213> ORGANISM: Homo sapiens

<400> SEQUENCE: 3
aacttatgtg tgacatgttc taat                                    24

<210> SEQ ID NO 4
<211> LENGTH: 25
<212> TYPE: DNA
<213> ORGANISM: Homo sapiens

<400> SEQUENCE: 4
aaccttatgt gtgacatgtt ctaat                                   25

<210> SEQ ID NO 5
<211> LENGTH: 25
<212> TYPE: DNA
<213> ORGANISM: Homo sapiens

<400> SEQUENCE: 5
aaccttatgt gtgacatgtt ctaat                                   25

<210> SEQ ID NO 6
<211> LENGTH: 22
<212> TYPE: DNA
<213> ORGANISM: Homo sapiens
```

```
<400> SEQUENCE: 6
aaggcactct tgcctacgct aa                                    22

<210> SEQ ID NO 7
<211> LENGTH: 22
<212> TYPE: DNA
<213> ORGANISM: Homo sapiens

<400> SEQUENCE: 7
aaggcactct tgcctacgct at                                    22

<210> SEQ ID NO 8
<211> LENGTH: 23
<212> TYPE: DNA
<213> ORGANISM: Homo sapiens

<400> SEQUENCE: 8
cgtcaaggca ctcttgccta cct                                   23

<210> SEQ ID NO 9
<211> LENGTH: 22
<212> TYPE: DNA
<213> ORGANISM: Homo sapiens

<400> SEQUENCE: 9
aggcactctt gcctacgcta tt                                    22

<210> SEQ ID NO 10
<211> LENGTH: 20
<212> TYPE: DNA
<213> ORGANISM: Homo sapiens

<400> SEQUENCE: 10
gcactcttgc ctacgccata                                       20

<210> SEQ ID NO 11
<211> LENGTH: 22
<212> TYPE: DNA
<213> ORGANISM: Homo sapiens

<400> SEQUENCE: 11
aaggcactct tgcctacgct ag                                    22
```